United States Patent [19]

Umezawa et al.

[11] Patent Number: 4,855,414

[45] Date of Patent: Aug. 8, 1989

[54] PROCESS FOR PRODUCTION OF ANTHRACYCLINE COMPOUND R20X2

[75] Inventors: Hamao Umezawa; Kazuo Umezawa, both of Tokyo; Atsuo Odagawa, Maebashi; Shiro Kataoka, Maebashi; Shohachi Nakajima, Maebashi, all of Japan

[73] Assignee: Kirin Beer Kabushiki Kaisha, Tokyo, Japan

[21] Appl. No.: 68,627

[22] Filed: Jun. 30, 1987

[30] Foreign Application Priority Data

Jul. 4, 1986 [JP] Japan .................. 61-157359

[51] Int. Cl.$^4$ ........................... C07H 15/24
[52] U.S. Cl. .................. 536/6.4; 260/351.4; 260/351.5
[58] Field of Search ............ 260/351.4, 351.5; 536/6.4; 568/801, 836

[56] References Cited

U.S. PATENT DOCUMENTS

| | | | |
|---|---|---|---|
| 3,862,225 | 1/1975 | Conover et al. | 260/351.5 |
| 4,263,428 | 4/1981 | Apple et al. | 536/6.4 |
| 4,612,371 | 9/1986 | Yoshimoto et al. | 536/6.4 |

OTHER PUBLICATIONS

Mar., *Advanced Organic Chemistry*, 1977 2 ed., pp. 356–357.

Primary Examiner—Richard L. Raymond
Assistant Examiner—Raymond Covington
Attorney, Agent, or Firm—Ladas & Parry

[57] ABSTRACT

An anthracycline compound, R20X2, of the following formula (II) is produced by a process which comprises subjecting an anthracycline compound, R20X3, of the following formula (I) or a salt thereof to reaction in the co-presence of (1) acetone and/or dimethylformamide and (2) an aqueous solution containing ammonium ion and/or trialkylamine.

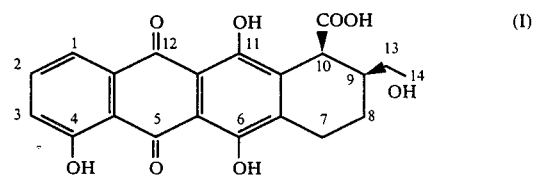

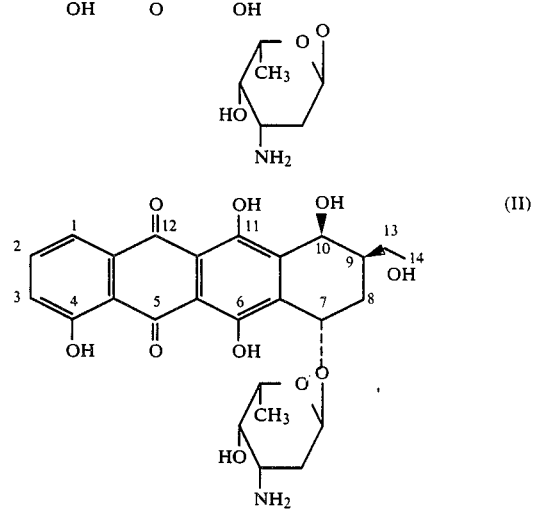

The anthracycline compound, R20X2, can be produced not only by the cultivation of actinomycetes but also, in accordance with the process as shown above, by chemical conversion of the anthracycline compound, R20X3, in a high yield.

1 Claim, No Drawings

PROCESS FOR PRODUCTION OF ANTHRACYCLINE COMPOUND R20X2

BACKGROUND OF THE INVENTION

The present invention relates to a process for producing an anthracycline compound, R20X2 (13-deoxo-10-hydroxycarminomycin, hereinafter referred to as R20X2), which is useful as an antitumor antibiotic.

We have already found R20X2 in the culture broth of actinomycetes and applied for patents (Japanese Patent Laid-Open Pub. Nos. 33194/1986 and 76498/1986). In both patent applications, R20X2 was isolated from the culture broth of a microorganism. While methods based on the cultivation of microorganisms are per se useful, a more efficient method, if developed, would be advantageous as a matter of course.

One of the co-inventors of the present invention has also found in the culture broth of actinomycetes an anthracycline compound, R20X3 (13-deoxo-10-hydroxycarbonylcarminomyin, hereinafter referred to as R20X3), which can be a starting compound for the R20X2 of the present invention, and again applied for a patent (Japanese Patent Laid-Open Pub. No. 8300/1985).

SUMMARY OF THE INVENTION

The present invention provides a process for producing R20X2 more efficiently.

More particularly, the process for producing the anthracycline compound, R20X2, of the following formula (II) according to this invention comprises subjecting the anthracycline compound, R20X3, of the following formula (I) or a salt thereof to reaction in the co-presence of (1) acetone and/or dimethylformamide and (2) an aqueous solution containing ammonium ion and/or trialkylamine.

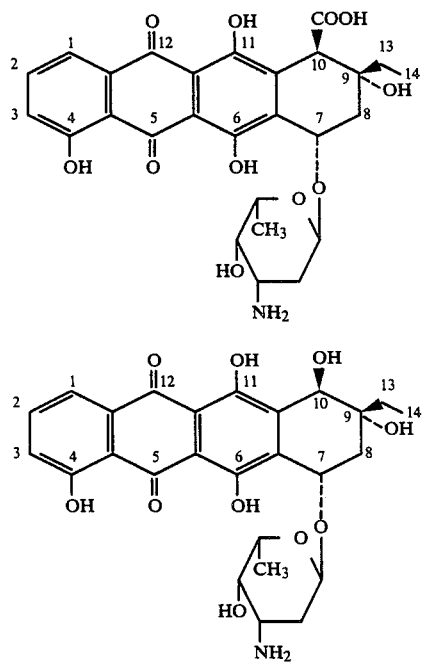

The anthracycline compound, R20X2, can be produced not only by the cultivation of actinomycetes but also, in accordance with the present invention, by chemical conversion of the anthracycline compound, R20X3. The chemical conversion of the R20X3 in this case can be carried out very readily with respect to the species of reagents as well as the reaction conditions while ensuring a good yield, and the starting compound R20X3 can be obtained by a simple microbiological method. For these reasons, it can be said that the R20X2 has been made more readily available.

DETAILED DESCRIPTION OF THE INVENTION R20X3

The R20X3 used in the present invention is a known substance and can be produced by the method described in Japanese Patent Laid-Open Pub. No. 8300/1985 mentioned previously.

Salts of the R20X3 include acid addition salts and alkali salts. Specific examples of the former salts are inorganic acid salts with hydrochloric acid, sulfuric acid, and phosphoric acid and organic acid salts with acetic acid, lactic acid, propionic acid, maleic acid, oleic acid, palmitic acid, citric acid, succinic acid, tartaric acid, fumaric acid, glumtamic acid, pantothenic acid, and lauryl sulfonate, while examples of the latter salts are alkali salts such as sodium, pottasium and calcium.

Reaction Conditions

In the present invention, the R20X2 is produced by subjecting the R20X3 or a salt thereof to reaction in the co-presence of (1) acetone and/or dimethylformamide and (2) an aqueous solution containing ammonium ion and/or trialkylamine, and the particular reaction conditions required are as follows.

The method of bringing the above mentioned components into co-presence is not particularly limited, and any method suitable for the purpose can be employed. For example, the R20X3 is dissolved in an aqueous solution containing ammonium ion and/or trialkylamine, and acetone and/or dimethylformamide may be added thereto. Preferably, the reaction system is a homogeneous solution.

The quantities of the respective components used are not critical and can be selected suitably. For reaction efficiency, however, the following conditions are generally preferred.

(1) The R20X3 or a salt thereof is used in such a quantity that the same can be dissolved in an aqueous solution containing ammonium ion and/or trialkylamine.

(2) 10 mols or more ammonium ion and/or trialkylamine are/is used per mol of the R20X3 or a salt thereof.

(3) 2 to 100 volumes of acetone and/or dimethylformamide are/is used per volume of an aqueous solution containing ammonium ion and/or trialkylamine.

For the source of ammonium ion, aqueous ammonia or ammonium salts such as ammonium chloride, ammonium carbonate, and ammonium acetate can be used. For the trialkylamine, tri-lower alkylamine such as trimethylamine, triethylamine, diisopropylethylamine, tripropylamine, and tributylamine can be used particularly preferably. These are just typical examples, and any other compounds suitable for the purpose can be employed.

A suitable reaction temperature is in the range of from the solidifying point to the boiling point of the reaction system, a temperature around room temperature (0° C.-30° C.) being particularly suitable.

Under the above stated reaction conditions, the reaction of converting the hydroxycarbonyl group in the R20X3 into the hydroxyl group can be terminated within several minutes to several days.

The reaction mixture obtained by the method of the present invention can be purified to isolate a desired compound, R20X2, by a known purification procedure employed in the preparation of anthracycline, for example, chromatography using silica gel.

The reaction according to this invention ensures an increased yield when it is carried out in the copresence of molecular oxygen and therefore is particularly preferably performed under aeration.

This reaction is desirably carried out with all the reactants in solution state as has been indicated hereinbefore. It is also possible, however, to cause a suitable column to adsorb the starting compound R20X3 and to treat the column with acetone and/or dimethylformamide and aqueous ammonia and/or trialkylamine as eluents to elute the R20X3 as R20X2. This embodiment is also included in the present invention.

EXAMPLE 1

100 mg of R20X3 was dissolved in 3 ml of 2.8% aqueous ammonia. 15 ml of acetone was added to the solution, and the mixture was left standing at room temperature (20° C.) for one hour. The resultant mixture was concentrated to dryness and subjected to silica gel column chromatography by using a 10:1 chloroform-methanol system to obtain 47.4 mg of R20X2. In this Example, the starting compound R20X3 had been prepared in accordance with the method described in Japanese Patent Laid-Open Pub. No. 8300/1985 (similarly as in Examples 2 and 3).

EXAMPLE 2

100 mg of R20X3 was dissolved in 3 ml of a triethylamine solution, and to this solution was added 15 ml of dimethylformamide. The resultant solution was left standing at room temperature (20° C.) for one hour. The reaction solution was concentrated to dryness and subjected to silica gel column chromatography by using a 10:1 chloroform-methanol system to obtain 46.0 mg of R20X2.

EXAMPLE 3

100 mg of R20X3 was dissolved in 3 ml of 2.8% aqueous solution of ammonium carbonate, and to this solution was added 15 ml of acetone. The resultant solution was left standing at room temperature (20° C.) for one hour. The reaction solution was concentrated to dryness and subjected to silica gel column chromatography by using a 10:1 chloroform-methanol system to obtain 52.8 mg of R20X2.

EXAMPLE 4

(1) Preparation of culture fluid containing R20X3

The culture fluid was prepared from strain R20 (FERM BP-945 (FERM P-7138)) in the following manner.

(a) Inoculum Preparation

The culture medium used was prepared by dissolving the following ingredients in 1 liter of water and adjusting the pH of the solution to 7.2.

Polypeptone, 1%
Molasses, 1%
Meat extract, 1%

100 ml of the medium thus prepared was sterilized in a 500-ml Erlenmeyer flask and inoculated with a loopful of spores collected from a slant culture of strain R20. The inoculated medium was subjected to shake culture for 5 days at 27° C. on a rotary shaker (200 r.p.m.) to prepare an inoculum.

(b) Cultivation

A fermentation medium was prepared by dissolving the following ingredients in 1 liter of water and adjusting the pH of the resultant solution to 6.5.

Glucose, 0.5%
Corn steep liquor, 1.5%
Soybean meal, 1.5%
Maltose, 4.0%
Dry yeast, 0.2%
Calcium carbonate, 0.4% (precipitated)

25 liters of the fermentation medium was sterilized in a 50-l jar fermenter, and 3 vials of the inoculums prepared as described above were added to the sterilized medium. Fermentation was carried out for 7 days at 27° C. at 1 v.v.m. and 200 r.p.m.

(c) Treatment of R20X3

The fermented mash was adjusted to pH 10 and filtered to separate cells from the filtrate. The filtrate was adjusted to pH 2, and the precipitate formed was subjected to centrifugation. The precipitate fraction was dried to obtain 7.9 g of crude R20X3 powder.

7.9 g of the crude R20X3 powder obtained by centrifugation was dissolved in 1 liter of 2.8% aqueous ammonia, and 5 liters of acetone was added thereto. The resulting solution was left standing at room temperature for 2 hours and then concentrated.

The residue from the concentration was extracted three times with a 10:1 chloroform-methanol solvent mixture. The chloroform-methanol layer was dehydrated with sodium sulfate anhydride and then concentrated. The product obtained was subjected to silica gel column chromatography by using a 10:1 chloroform-methanol system to obtain 0.75 g of R20X2.

R20X3 which remained dissolved in the supernatant formed when the fermented mash was subjected to centrifugation, on the other hand, was adsorbed onto a resin "Diaion HP20" (supplied by Mitsubishi Kasei K.K., Japan). The R20X3 thus adsorbed was washed with water and eluted with a 2.8% aqueous ammonia-acetone (1:5) solution mixture (which corresponds to a reactant mixture in the present invention). The colored eluate was concentrated, and the residue from the concentration was neutralized with 1N hydrochloric acid and extracted three times with a 10:1 chloroform-methanol solvent mixture. The chloroform-methanol layer was dehydrated with sodium sulfate anhydride and then concentrated to dryness. The product obtained was subjected to silica gel column chromatography by using a 10:1 chloroform-methanol system to obtain 1.35 g of R20X2.

What is claimed is:

1. A process for producing an anthracycline compound, R20X2, of the following formula (II), which comprises subjecting an anthracycline compound, R20X3, of the following formula (I) or a salt thereof to reaction in the co-presence of (1) acetone and/or dimethylformamide and (2) an aqueous solution containing ammonium ion and/or trialkylamine in a temperature range of about 0° C. to about 30° C.

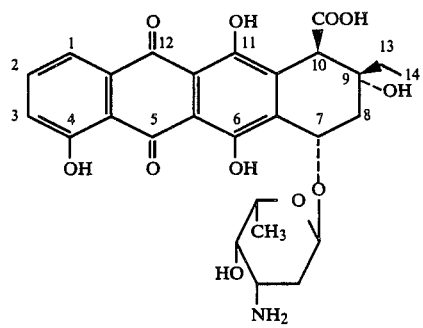 (I)
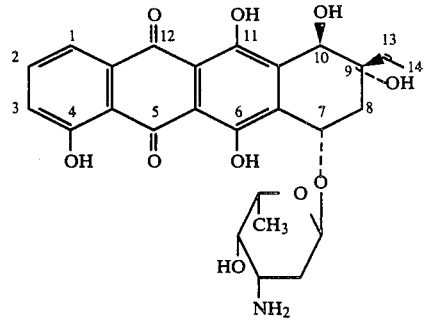 (II)
* * * * *